US011266764B2

(12) United States Patent
Frey et al.

(10) Patent No.: US 11,266,764 B2
(45) Date of Patent: Mar. 8, 2022

(54) NON-UNIFORMLY STIFF POLYMERIC SCAFFOLDS AND METHODS FOR PRODUCING THEREOF

(71) Applicant: REGENOSCA SA, Lausanne (CH)

(72) Inventors: Peter Frey, Epalinges (CH); Jeffrey A. Hubbell, Chicago, IL (US); Hans M. Larsson, Lausanne (CH); Elif Vardar, Lausanne (CH); Eva-Maria Balet, Cressier (CH); Ganesh Vythilingam, Lausanne (CH); Kalitha Pinnagoda, St-Légier (CH)

(73) Assignee: Regenosca SA, Lausanne (CH)

( * ) Notice: Subject to any disclaimer, the term of this patent is extended or adjusted under 35 U.S.C. 154(b) by 198 days.

(21) Appl. No.: 16/092,953

(22) PCT Filed: Mar. 29, 2017

(86) PCT No.: PCT/IB2017/051796
§ 371 (c)(1),
(2) Date: Oct. 11, 2018

(87) PCT Pub. No.: WO2017/178915
PCT Pub. Date: Oct. 19, 2017

(65) Prior Publication Data
US 2019/0117838 A1 Apr. 25, 2019

(30) Foreign Application Priority Data

Apr. 13, 2016 (WO) ............... PCT/IB2016/052096

(51) Int. Cl.
A61L 27/36 (2006.01)
A61L 27/24 (2006.01)
A61L 27/20 (2006.01)
A61L 27/22 (2006.01)
A61L 27/52 (2006.01)
A61L 27/54 (2006.01)
C08J 3/075 (2006.01)
C08L 89/00 (2006.01)

(52) U.S. Cl.
CPC .......... A61L 27/3633 (2013.01); A61L 27/20 (2013.01); A61L 27/222 (2013.01); A61L 27/225 (2013.01); A61L 27/24 (2013.01); A61L 27/52 (2013.01); A61L 27/54 (2013.01); C08J 3/075 (2013.01); C08L 89/00 (2013.01); C08J 2389/00 (2013.01); C08L 2203/02 (2013.01)

(58) Field of Classification Search
CPC ........ A61L 27/24; A61L 27/222; C08J 3/075; C08L 2203/02; C08L 89/00
See application file for complete search history.

(56) References Cited

U.S. PATENT DOCUMENTS 5,567,806 A 10/1996 Abdul-Malak et al.
2008/0131473 A1* 6/2008 Brown .................... A61L 27/52
424/423

FOREIGN PATENT DOCUMENTS

| EP | 1098024 A1 | 5/2001 | |
| EP | 1 561 480 | 12/2015 | |
| EP | 3165240 A1 | 5/2017 | |
| GB | WO2006/003442 | * 1/2006 | ............ A61L 27/00 |
| WO | WO 00/29484 | 5/2000 | |
| WO | 2006/003442 | 1/2006 | |
| WO | WO 2007/082295 | 7/2007 | |
| WO | WO 2012/004564 | 1/2012 | |

OTHER PUBLICATIONS

Skopinska-Wisniewska et al. (Materials Science and Engineering C 40 (2014) 66-70) (Year: 2014).*
Abou Neel et al., "Use of multiple unconfined compression for control of collagen gel scaffold density and mechanical properties" Soft Matter, vol. 2: 986-992 (2002).
Brown et al., "Ultrarapid Engineering of Biomimetic Materials and Tissues: Fabrication of Nano- and Microstructures by Plastic Compression" Advanced Functional Materials, vol. 15: 1762-1770 (2005).
Engler et al., "Myotubes differentiate optimally on substrates with tissue-like stiffness: pathological implications for soft or stiff microenvironments" The Journal of Cell Biology, vol. 166, No. 6: 877-887 (2004).
Gross, "The Heat Precipitation of Collagen from Neutral Salt Solutions: Some Rate-Regulating Factors" J. Biol. Chem., vol. 233, No. 2: 355-360 (1958).
Huebsch et al., "Harnessing Traction-Mediated Manipulation of the Cell-Matrix Interface to Control Stem Cell Fate" Nat Mater, vol. 9, No. 6: 518-526 (Jun. 2010).
Kawazoe et al., "A Cell Leakproof PLGA-Collagen Hybrid Scaffold for Cartilage Tissue Engineering" Biotechnol. Prog., vol. 26, No. 3: 819-826 (2009).
Lu et al., "PLLA-collagen and PLLA-gelatin hybrid scaffolds with funnel-like porous structure for skin tissue engineering" Sci. Technol. Adv. Mater., vol. 064210: 9 pages (2012).

(Continued)

Primary Examiner — Anna R Falkowitz
(74) Attorney, Agent, or Firm — Andre Roland S.A.; Nikolaus Schibli

(57) ABSTRACT

The invention relates to methods for producing a polymeric scaffold for use in tissue engineering applications or soft tissue surgery, as well as to the produced scaffolds and an associated kit. The method features a first fast drying step of applying a mechanical compression on a polymeric gel layer and a second slow drying step of the gel up to reach a polymer mass fraction of at least 60% w/w in the final scaffold. The method allows the production of scaffolds with high regeneration and healing properties of a grafted tissue via host cell invasion and colonization, and a good suturability. These goals are achieved through the formation within the scaffold of a non-uniform architecture creating softer and stiffer areas, which is maintained even upon re-swelling of the scaffold upon hydration of the final dried product.

11 Claims, 10 Drawing Sheets

(56) References Cited

OTHER PUBLICATIONS

Paul et al., "Chemical Stabilisation of Collagen as a Biomimetic" *The Scientific World Journal*, vol. 3: 138-155 (2003).
Petite, "Cytocompatibility of calf pericardium treated by glutaraldehyde and by the acyl azide methods in an organotypic culture model" *Biomaterials*, vol. 16: 1003-1008 (1995).
International Search Report for PCT/IB2017/051796 dated Sep. 21, 2017, 4 pages.
Written Opinion of the ISA for PCT/IB2017/051796 dated Sep. 21, 2017, 5 pages.

* cited by examiner

NON-UNIFORMLY STIFF POLYMERIC SCAFFOLDS AND METHODS FOR PRODUCING THEREOF

This application is the U.S. national phase of International Application No. PCT/IB2017/051796 filed Mar. 29, 2017 which designated the U.S. and claims priority to International Application No. PCT/IB2016/052096 filed Apr. 13, 2016, the entire contents of each of which are hereby incorporated by reference.

TECHNICAL FIELD

The invention relates to tissue engineering, diagnostics and surgery, particularly to non-uniformly stiff polymeric scaffolds and methods for producing such objects.

BACKGROUND ART

Collagen is one of the first natural polymers used as a biomaterial. Being the most abundant structural extracellular matrix protein in the human body, it is therefore widely used as a scaffold component for tissue engineering applications, and considered among the first choices for natural scaffold materials.

Collagen gels are formed by a process called fibrillogenesis. Fibrillogenesis starts when a diluted acidic collagen solution is adjusted in vitro to physiological pH and temperature (Gross and Kirk, J. Bio. Chem 233 (1958): 355-360). Collagen gels are interesting as scaffolds due to their good biocompatibility, their low immunogenicity and their easy of remodelling by cells. However, the large excess of fluid entrapped between the collagen fibers render them inherently weak and thus difficult to manipulate. Several strategies were proposed to obtain collagen scaffolds having improved mechanical properties. The simple culturing of cells within collagen gels results in the expulsion of some of the interstitial fluid by gel contraction, but cell compaction is a not an easily controllable process and the increase in collagen density is linked to a reduction of the scaffold surface (i.e. scaffold shrinkage). Cross-linking of the collagen fibers enhances the mechanical properties of collagen scaffolds without changing the scaffold surface. Physical, chemical and biological collagen cross-linking methods are well reported in literature (Paul and Bailey, The Scientific World Journal 3 (2003): 138-155). One option is the lyophilization (freeze-drying) of an aqueous collagen solution followed by chemical cross-linking (EP1561480). Another possibility is freeze-drying of a collagen gel followed by thermal dehydration cross-linking (EP1098024).

The most common aldehyde cross-linking agent is glutaraldehyde. However its use for medical applications is questioned due to its cytotoxicity. Several chemical cross-linking agents have been identified that achieve comparable cross-linking levels to that of glutaraldehyde while improving the cytocompatibility (i.e. diphenylphosphoryl azide, 1-ethyl-3-(3-dimethylaminopropyl)carbodiimide, genipin) (Petite H. et al., Biomaterials 16 (1995): 1003-1008).

Another method to produce collagen gels with enhanced mechanical properties consists of applying plastic compression. During the process of plastic compression, the interstitial liquid is expelled from a collagen gel and does not return on removal of the load. This simple, fast, controllable, and cell-friendly process to engineer collagen matrices with suitable mechanical properties for soft tissue engineering was described in detail by Brown and colleagues (WO 2006/003442; WO 2012/004564; Abou Neel E. A. et al., Soft Matter 2 (2006): 986-992; Brown R. A. et al., Adv Funct Mater 15 (2005): 1762-1770). Furthermore, collagen hybrid structures have been reported where a synthetic polymer component provided the mechanical support (Kawazoe N. et al., Biotechnol Prog 26 (2010): 819-826; Lu H. et al., Sci Technol Adv Mater 13 (2012)). However, this approach decreases the biocompatibility of the matrix.

Most scaffold design strategies aim to mimic the mechanical properties of the native tissue as much as possible while also providing a scaffold that is easy to handle and suturable. The following suturable collagen matrices were reported in literature: collagen sponge or collagen/glycosaminoglycan sponge crosslinked with collagen gel (U.S. Pat. No. 5,567,806), double layered collagen matrix resulting from a casting, freeze-drying, and lyophilisation procedure where the collagen layers differ in density (WO 2007/082295), and a high density freeze-dried collagen matrix (WO 2000/029484).

Furthermore it is well known that the mechanical properties of a scaffold influences cell behaviour. Myogenesis is best achieved on collagen scaffolds that are moderately stiff (Engler A. J. et al., J Cell Biology 166 (2004): 877-887) while osteogenesis is achieved on stiff collagen scaffolds (Huebsch N. et al., Nat Matter 9 (2010): 518-526). Researchers can change mechanical properties of collagen hydrogels by varying collagen concentration and using different cross-linking methods. However, these scaffolds are uniform matrices and a soft collagen scaffold showing excellent cell behaviour in term of proliferation and differentiation might not be suitable for a clinical application (i.e. not suturable, difficult to handle).

SUMMARY OF INVENTION

In order to address and overcome the drawbacks associated with the prior art solutions concerning polymeric products for tissue engineering and surgery, the inventors developed a brand new method for producing polymeric scaffolds displaying several advantages when used in an in vivo approach. Particularly, the scaffold of the present invention features superior properties in terms of resistance upon suture when grafted in vivo in/on soft tissues, while exhibiting at the same time excellent mechanical and functional properties in terms of facilitation of host cell infiltration upon grafting, reduced inflammatory reactions/rejection and improved tissue healing, with associated faster recovery of a subject undergone to a surgical operation. The scaffold of the invention can be stored off-the-shelf, thus reducing the costs associated to the surgery, and providing successful grafting results even in a cell-free scenario. In a particular aspect, the present invention proposes an easy and controllable process to provide non-uniformly stiff polymeric scaffolds that consists of denser areas ensuring suturability and easy handling for the surgeons, as well as softer zones to induce the appropriate cell behaviour and fate in term of cell proliferation and differentiation.

Accordingly, it is an object of the present invention to provide a method for producing a non-uniformly stiff polymeric scaffold for use in tissue engineering, diagnostics or surgical procedures, characterized in that it comprises the following steps:
  a) providing at least one layer of a polymeric material gel;
  b) performing a first fast drying step by applying a mechanical compression on said polymeric material gel layer; and c) performing a second slow drying step of the gel up to reach a polymeric material mass fraction of at least 60% w/w.

In one embodiment, the method is followed by a hydration step where the scaffold re-swells with more than 4% w/w.

In one embodiment, the method is characterized in that step c) is performed by water filtration means, air-drying or any combination thereof.

In a particular embodiment, the method is characterized in that water filtration is performed by dialysis.

In a particular embodiment, the method is characterized in that air-drying is performed under gravity for at least 1 hour.

In one embodiment, the method further comprises the step of circumferentially wrapping the polymeric scaffold around a support in order to have a tubular polymeric scaffold comprising a lumen.

In one embodiment, the method comprises step a') instead of step a) of pouring a polymeric gel precursor solution into a substantially cylindrical mould comprising therein a coaxial elongated support for creating a tubular single layer of polymeric material gel.

In one embodiment, the method is characterized in that the polymeric scaffold is cell-free.

In one embodiment, the method is characterized in that the polymeric material is natural polymeric material or an extra-cellular matrix (ECM)-derived polymeric material.

In one embodiment, the method is characterized in that the natural polymeric material or ECM-derived polymeric material is gelatin, elastin, collagen, agar/agarose, chitosan, fibrin, proteoglycans, a polyamino-acid or its derivatives, preferably polylysin or gelatin methyl cellulose, carbomethyl cellulose, polysaccharides and their derivatives, preferably glycosaminoglycanes such as hyaluronic acid, chondroitinsulfate, dermatansulfate, heparansulfate, heparine, keratansulfate or alginate, or any combination of the foregoing.

In one embodiment, the method is characterized in that no crosslinkers are added to the polymeric material gel.

In a particular embodiment, the method is characterized in that the polymeric gel of step a) is obtained from a collagen gel precursor solution having a collagen concentration of at least 2.1 mg/mL, preferably between 2.5 and 40 mg/mL.

A further aspect of the invention relates to a method for producing a non-uniformly stiff polymeric scaffold for use in tissue engineering, diagnostics or surgical procedures, characterized in that it comprises the following steps:
a) providing a single layer of a mechanically compressed polymeric material gel wrapped around a support;
b) dipping a portion of the support-wrapped polymeric gel layer into an aqueous solution while leaving another portion air-drying under gravity for a certain amount of time;
c) flipping the polymeric gel layer portion previously dipped into the aqueous solution onto the air-dried portion; and
d) optionally air-drying under gravity both layers for a certain amount of time wherein at least one layer of the so obtained polymeric scaffold has a polymer mass fraction of at least 60% w/w.

In one embodiment, said method comprises step a') instead of step a) of pouring a polymeric gel precursor solution into a substantially cylindrical mould comprising therein a coaxial elongated support for creating a tubular single layer of polymeric gel, gelling it and mechanically compress it.

In one embodiment, the method is characterized in that the polymeric scaffold is cell-free.

In one embodiment, the method is characterized in that the polymeric material is natural polymeric material or an extra-cellular matrix (ECM)-derived polymeric material.

In one embodiment, the method is characterized in that the natural polymeric material or ECM-derived polymeric material is gelatin, elastin, collagen, agar/agarose, chitosan, fibrin, proteoglycans, a polyamino-acid or its derivatives, preferably polylysin or gelatin methyl cellulose, carbomethyl cellulose, polysaccharides and their derivatives, preferably glycosaminoglycanes such as hyaluronic acid, chondroitinsulfate, dermatansulfate, heparansulfate, heparine, keratansulfate or alginate, or any combination of the foregoing.

In one embodiment, the method is characterized in that no crosslinkers are added to the polymeric material gel.

In a particular embodiment, the method is characterized in that the polymeric gel of step a) is obtained from a collagen gel precursor solution having a collagen concentration of at least 2.1 mg/mL, preferably between 2.5 and 40 mg/mL.

A further aspect of the present invention relates to a non-uniformly stiff polymeric scaffold for use in tissue engineering, diagnostics or surgical procedures produced according to the previously-described methods, said scaffold being characterized in that it has at least a polymeric material layer having a polymer mass fraction of at least 52% w/w at steady state upon re-swelling, with a denser polymeric structure at the surface and less dense in the core of the scaffold.

In one embodiment, the non-uniformly stiff polymeric scaffold is characterized in that it is suturable.

In one embodiment, the non-uniformly stiff polymeric scaffold is characterized in that it is at least 1 cm long.

In one embodiment, the non-uniformly stiff polymeric scaffold is characterized in that it comprises a bioactive agent.

Another object of the present invention relates to a kit comprising:
a) a container;
b) an aqueous solution; and
c) the non-uniformly stiff polymeric scaffold as previously described.

In one embodiment, the kit is characterized in that is sterilized through electrode beam, gamma-rays radiation or X-rays radiation.

DESCRIPTION OF EMBODIMENTS

Figure 1:
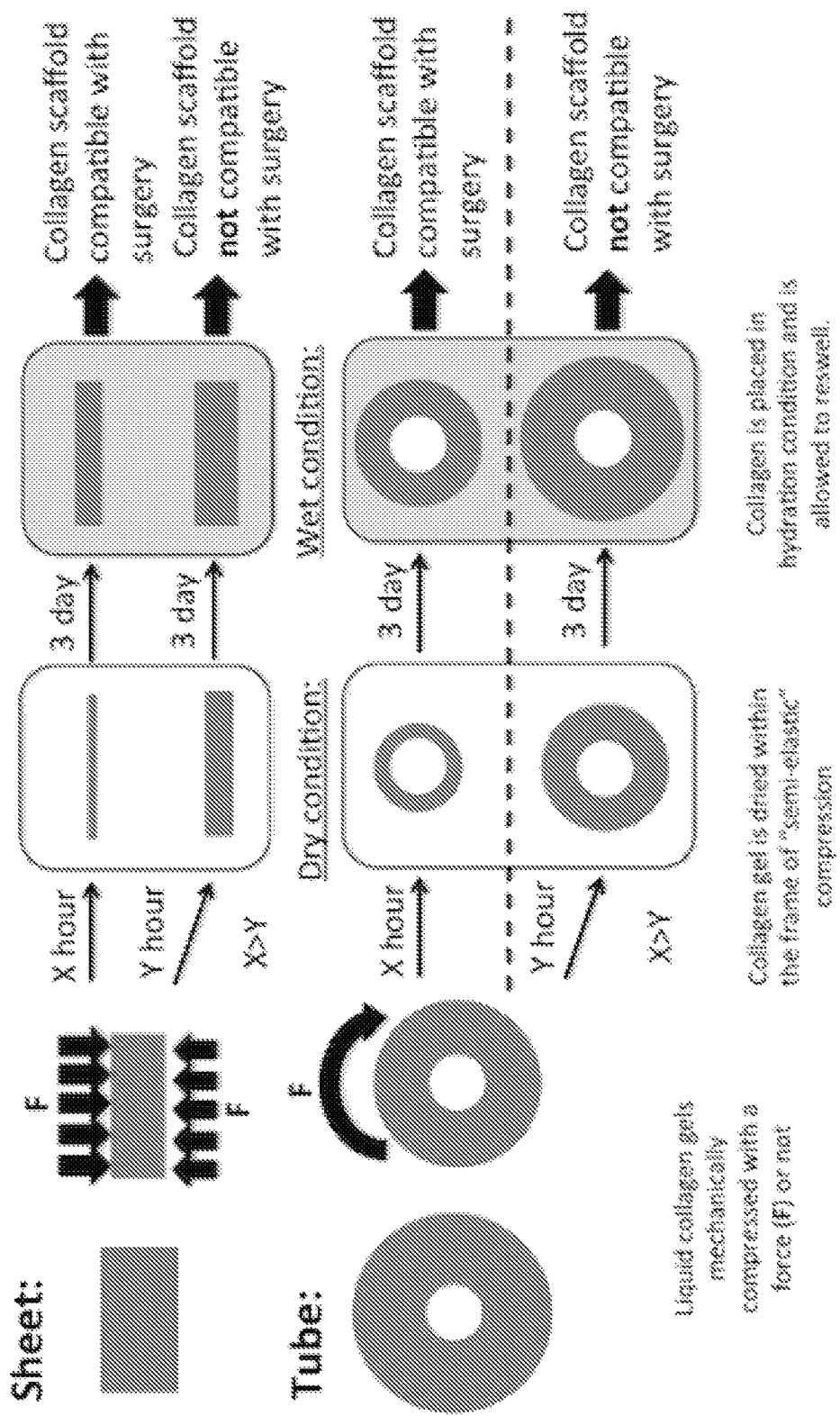
FIG. 1 depicts a sketch of the method of the invention for the production of sheets (1A) or tubes (1B) of a non-uniformly stiff polymeric scaffold.

The present disclosure may be more readily understood by reference to the following detailed description presented in connection with the accompanying drawing figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a", "an" and "the" include plural referents unless the context clearly dictates otherwise. Thus, for example, reference to "a bioactive agent" includes a plurality of such agents and reference to "a layer" includes reference to one or more layers, and so forth.

Also, the use of "or" means "and/or" unless otherwise stated. Similarly, "comprise", "comprises", "comprising", "include", "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of".

The main object of the present invention relies at least in part on a novel method for producing a polymeric material scaffold for use in tissue engineering or surgical procedures, as well as for diagnostics and basic research, having very peculiar mechanical and functional characteristics. In fact, once produced with the methods according to the invention, the scaffolds of the invention surprisingly show a non-uniform architecture, wherein some zones within the polymeric scaffold display differences in polymer density and therefore also in stiffness. Since there is a close relation between the polymer concentration and the mechanical properties of the scaffold such as stiffness and elasticity, this feature advantageously guide cell migration, proliferation and differentiation in vivo thanks to the presence of one or more less dense polymeric area that can be easily remodeled by invading host cells, thus enhancing the tissue regeneration capacity of the scaffold, while keeping at the same time a portion of the scaffold with a sufficient mechanical strength for being sutured during surgery.

The method of the invention covers two main approaches for the manufacturing of the non-uniformly stiff polymeric scaffolds of the invention. Contrary to some prior art approaches involving a process of plastic compression for creating uniform polymer (e.g. collagen) matrices, the present method exploits a new method renamed by the inventors "semi-elastic compression" of polymeric gels. In contrast to an elastic compression, where the polymeric gel swells back to their initial state after removal of the compressive force applied therein, the gels processed according to the present method swell back only to an intermediate state, which is dependent on the initial polymer concentration and the final dry state. Surprisingly, these semi-elastic compressed and rehydrated polymeric structures are stable enough to be easily handled and to be sutured in an in vivo surgical approach. This is realized by applying a first fast mechanical compression step using mechanical load followed by a slow drying phase, preferably followed by a final rehydration.

The invention will be better understood with the help of the following definitions.

As used herein, a "polymeric material" is any material comprising polymers, large molecules (also known as macromolecules) composed of many repeated smaller units, or subunits, called monomers, tightly bonded together preferably by covalent bonds. Polymer architecture at the molecular scale can be rather diverse. A linear polymer consists of a long linear chain of monomers. A branched polymer comprises a long backbone chain with several short side-chain branches covalently attached. Cross-linked polymers have monomers of one long or short chain covalently bonded with monomers of another short or long chain. Cross-linking results in a three-dimensional molecular network; the whole polymer is a giant macromolecule. Another useful classification of polymers is based on the chemical type of the monomers: homopolymers consist of monomers of the same type, copolymers have different repeating units. Furthermore, depending on the arrangement of the types of monomers in the polymer chain, there are the following classification: the different repeating units are distributed randomly (random copolymer) or there are alternating sequences of the different monomers (alternating copolymers) in block copolymers long sequences of one monomer type are followed by long sequences of another type; and graft copolymers consist of a chain made from one type of monomer with branches of another type. A sufficiently dense polymer solution can be crosslinked to form a polymer gel, including a hydrogel or a cryogel, which is a soft solid.

Polymer materials may also be formed by blending two or more polymers into physical mixtures. For example, the poor impact strength of a polymer can be greatly improved by incorporating small particles of an elastomer. Many properties of polymeric materials depend on the microscopic arrangement of their molecules. Polymers can have an amorphous (disordered) or semicrystalline (partially crystalline, partially ordered) structure. Polymers can be mixed with inorganic particles (usually in the form of continuous fibres, such as glass or particulates such as mica, talc and clay) in order to modify and improve (mainly but not exclusively) their mechanical properties.

Suitable polymeric materials include, but are not limited to, synthetic polymers such as polyurethanes, poly-olefins, polyethylene glycol (PEG), poly(glycolide) (PGA), poly(L-lactide) (PLA) or poly(lactide-co-glycolide) (PLGA); natural polymeric materials (i.e., non-synthetic polymers, polymers that can be found in nature) and/or polymers derived from the extracellular matrix (ECM) as gelatin, laminin, elastin, collagen, agar/agarose, chitosan, fibrin, proteoglycans, a polyamino-acid or its derivatives, preferably polylysin or gelatin methyl cellulose, carboxymethylcellulose (CMC), polysaccharides and their derivatives, preferably glycosaminoglycanes such as hyaluronic acid, chondroitin-sulfate, dermatansulfate, heparansulfate, heparine, keratansulfate or alginate, nucleotides, polylipides, fatty acids, as well as any derivative thereof, fragment thereof and any combination of the foregoing. Natural and ECM-derived polymers are a first choice biomaterial for tissue engineering applications envisaged by the present disclosure, due to their biological and chemical similarities to natural tissues and the presence of biologically active sites in their structures. For example, collagen and hyaluronic acid can be considered as the most preferred embodiments for constituting the polymeric scaffolds of the invention.

As used herein, the term "gel" refers to a non-fluid colloidal network or polymer network that is expanded throughout its whole volume by a fluid. A gel is a solid three-dimensional network that spans the volume of a liquid medium and ensnares it through surface tension effects. The internal network structure may result from physical bonds (physical gels) or chemical bonds (chemical gels).

As used herein, the term "hydrogel" refers to a gel in which the swelling agent is water. A hydrogel is a macromolecular polymer gel constructed of a network of cross-linked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties.

Several physical properties of the (hydro)gels are dependent upon concentration. Increase in (hydro)gel concentration may change its pore radius, morphology, or its permeability to different molecular weight proteins. One skilled in the art will appreciate that the volume or dimensions (length, width, and thickness) of a (hydro)gel can be selected based on instant needs, such as for instance the region or environment into which a scaffold substantially made of an (hydro)gel is to be implanted.

For "collagen" is herein meant any kind of natural or recombinant collagen of animal origin, preferably mammals, such as bovine, porcine, rat, human and the like. Accordingly, collagen type 1 to 28 can be used in the frame of the present invention, as well as fragments thereof or any combinations of the foregoing. Collagen can also possibly derive from any body location of the said animals such as skin, intestine, cartilage and so forth, as long it fits with biocompatibility requirements or with translation into an in vivo approach. In a preferred embodiment, type 1 collagen of bovine origin is used.

The polymeric gel of the invention can be manufactured/processed through any suitable manufacturing method known in the art allowing to create a highly interconnected pore network in the material, such as e.g. (photo)lithography including two-photon lithography, casting and molding, 3D printing, inkjet printing, porogen leaching, emulsion freezing/freeze drying technique, inverse opal hydrogelation, cryogelation, electrospinning or fiber extrusion and bonding, gas foaming, thermally induced phase separation and so forth.

In one embodiment, the polymeric gel can be fabricated by top-down processes such as 3D printing. This technique allows full control over the distribution and size of pores and wall material in nearly arbitrary geometries, and therefore holds great possibilities in terms of organ-specific 3D design and fabrication.

In the frame of the present disclosure, a "scaffold" is any three dimensional material having a framework architecture, i.e. a support structure usually comprising hollow spaces within it. Generally speaking, a scaffold material is an artificial, usually temporary template structure capable of supporting three-dimensional body tissue/organ formation in vivo, ex vivo or in vitro. In this context, a scaffold material is also referred herewith as a "biomaterial" or "bioscaffold". A bioscaffold, inter alia, allows cell attachment and migration, delivers and retains cells and biochemical factors, enables diffusion of vital cell nutrients and expressed products, exerts certain mechanical and biological influences to modify the behaviour of the cells and so forth.

The scaffold material of the invention has been conceived and manufactured in order to act as a biocompatible, non-migratory and non-carcinogenic scaffolding agent. The general purpose was the development of a material having improved long-term efficacy, which can stimulate host cell infiltration and integrates with the surrounding tissue once implanted in a host, thus triggering neo-tissue formation via the promotion of a bioactive environment within the application site and giving rise to long-term functional repair. The scaffold material herein disclosed addresses and solves, among others, this problem.

The scaffold material is moreover, at least on some portions thereof, highly porous. In a preferred embodiment of the invention, the pores are all interconnected in order to create a continuous net of material that can act as a plausible physical support for other elements such as cells or bioactive agents, while providing at the same time additional key features to the scaffold such as its softness/stiffness, easiness of cell/tissue invasion and so forth. Accordingly, where present, pore diameters preferably comprised between about 0.2 and 200 µm in the less dense areas, with more preferred pore diameters comprised between about 0.5 and 10 µm. As will be evident to a person skilled in the art, these less dense areas within the scaffold are present, due to the non-uniform stiffness (and therefore density) of the scaffold itself, in the softer (and therefore, less dense) portion, while the stiffer (and therefore, denser) portion thereof is characterized by a negligible porosity, with pores, where present, with an average diameter of less than 0.2 µm. Moreover, it is preferred that the stiffer portion of the polymeric scaffold has a Young's modulus comprised between about 5 and 1500 kPa, whereas preferred Young's modulus values for the softer portion span between about 0.1 and about 20 kPa. In any embodiment, however, at least a 2.5 kPa difference in terms of Young's modulus between the softest and stiffest part of the scaffold is present.

In order to optimize the mechanical properties of the scaffold material of the invention and, in some aspects, its resorption/biodegradation rate, in preferred embodiments it is contemplated that the scaffold comprises a final polymer weight in a dried form of at least the 60% of the total scaffold weight (i.e. 60% w/w, also called mass fraction, wherein the remaining 40% or less is substantially composed of water or of an aqueous solution). A suitable polymer mass fraction depends on e.g. the molecular weight of the monomer, the nature of the monomer, the crosslinking strategy and the ratio of polymers. However, this value is tightly associated to the manufacturing steps of the method for producing said polymeric scaffold; in fact, as it will be more deeply detailed later on, the final polymer mass fraction in the scaffold can even be of at least 52% w/w upon re-swelling (re-hydration) of the scaffold in an aqueous solution, at the end of the production procedure.

Concerning the possible degradation/resorption rate of the scaffold upon in vivo application/implantation in a subject, this is mainly dependent on physico-chemical properties of the polymeric material of which it is composed of, as well as further factors such as crosslinking of the polymers, the polymer concentration, the site of implantation into a host and the like. The degradation/resorption rate can be calibrated by adjusting said physico-chemical parameters, such as for instance by polymer crosslinking, the use of inhibitor molecules, by changing the polymer density, crystallinity and/or its molecular weight distribution, changing the materials' porosity and so forth. Generally speaking, the scaffold material may be, at least in part and at least in some portion thereof, intrinsically biodegradable in vivo.

The scaffolds and the gels of the invention are preferably cell-free, but they can be seeded in vitro or in vivo with cells before, during and/or after their production. The scaffold, if to be used to transplant cells in a tissue engineering approach, comprises pores to permit the structure to be seeded with cells and e.g. to allow the cells to proliferate. For example, scaffolds are seeded by incubating the structure in a solution containing the cells for a suitable period of time. Alternatively, a multi-component scaffold is built in stages with each layer being seeded prior to laying down of another layer or before adherences of another pre-formed component. Alternatively, each compartment of the multi-compartment scaffold can be seeded separately. Different cell types, e.g., stem vs. differentiated, and/or with various phenotypes in terms of differentiation, activation, metabolic or functional state, can be seeded in the scaffold material. The scaffolds are suitable for use with any cell type, preferably forming soft tissues, which one may want to transplant. Such cells include but are not limited to, various stem cell populations (embryonic stem cells differentiated into various cell types), bone marrow or adipose tissue derived adult stem cells, mesenchymal stem cells, cardiac stem cells, pancreatic stem cells, neuronal cells, glial cells, spermatozoids and oocytes, endothelial progenitor cells, outgrowth endothelial cells, dendritic cells, hematopoietic stem cells, neural stem cells, satellite cells, side population cells. Such cells may further include but are not limited to, differentiated cell populations including osteoprogenitors and osteoblasts, chondrocytes, keratinocytes for skin, intestinal epithelial cells, smooth muscle cells, cardiac muscle cells, epithelial cells, endothelial cells, urothelial cells, fibroblasts, myoblasts, chondroblasts, osteoclasts, hepatocytes, bile duct cells, pancreatic islet cells, thyroid, parathyroid, adrenal, hypothalamic, pituitary, ovarian, testicular, salivary gland cells, adipocytes and combinations thereof. For example, smooth muscle cells and endothelial cells may be employed for muscular or tubular scaffolds, e.g., scaffolds intended as vascular, oesophageal, intestinal, rectal, or ureteral scaffolds; chondrocytes may be employed in cartilaginous scaffolds; cardiac muscle cells may be employed in heart scaffolds; hepatocytes and bile duct cells may be employed in liver scaffolds; myoblasts may be used in muscle regeneration; epithelial, endothelial, fibroblast, and nerve cells may be employed in scaffolds intended to function as replacements or enhancements for any of the wide variety of tissue types that contain these cells. In general, scaffolds of the invention may comprise any cell population competent to participate in regeneration, replacement or repair of a target tissue or organ, particularly (semi)soft or barely-reachable ones such as kidneys, brain, meninges, lungs, liver, stomach, sphincters, gut, bladder, ear tissues, cartilages, skin, pharynx, trachea, blood vessels, urethra, ureter, vagina, pelvic floor or pancreas.

Some mechanical/functional properties of the scaffold can be tailored according to the needs by changing the physical or chemical properties thereof (such as e.g. the collagen molecular chain length). Concerning collagen, in order to optimize these parameters and, in some aspects, the resorption/biodegradation rate, in preferred embodiments it is contemplated an average molecular weight for the collagen molecules substantially composing the scaffold comprised between about 30 and about 250 kDa. Concerning hyaluronic acid, an average molecular weight comprised between about 50 kDa and about 2 MDa is particularly preferred.

In most preferred embodiments, the final scaffold is not crosslinked or minimally crosslinked, in order to eliminating or reducing as much as possible e.g. the potential in vivo toxicity associated with some crosslinking agents such as glutaraldehyde. When a crosslinking process is used, crosslinking agents and their amount can be chosen at the operator's discretion, and a skilled in the art would easily envisage such parameters based on common practice. By practicing the production method of the invention that will be detailed later on, it is possible to produce scaffolds with such mechanical and functional properties to allow at the same time successful grafts in a host with ease suturability, without the impellent need of using crosslinking agents. For being considered successful, a graft should show no complications at the grafting site, such as no presence of opened structures as fistulae, strictures or stenoses, and/or the treated tissue/organ area should look histologically normal.

In some embodiments, the scaffold can be differentially permeable, allowing cell displacement only in certain physical areas thereof. The permeability of the scaffold composition is regulated, for example, by engineering the polymeric material for greater or smaller pore size, porosity, density, polymer cross-linking and/or viscoelasticity.

The scaffold material of the invention can be organized, during or after the production method, in a variety of geometric shapes such as beads, pellets, strip, block, toroid, capillary, patches, tubes, planar layers (e.g., thin sheets) and so forth, the final shape depending on the particular context it is to be used, and can comprise in some embodiments at least two areas or compartments having different structural/functional properties. For example, multicomponent scaffolds are constructed in e.g. concentric layers, each of which is characterized by different physico-chemical properties (% polymer, % crosslinking of polymer, chemical composition of scaffold, pore size and/or architecture, stiffness, porosity, presence or different concentration of bioactive agents and so on). Each niche can host one or more cell populations and/or have a specific effect on them, e.g., promoting or inhibiting a specific cellular function, proliferation, differentiation, migration and so forth. Such a configuration is particularly useful in maintaining for long time periods the "sternness" of a population of cells, while simultaneously pushing daughter cells to multiply rapidly and differentiate appropriately for participation in tissue regeneration.

A compartmentalization of the device can be obtained by rational design and fabrication processes using different compositions or concentrations of compositions for each compartment. For example, a stem cell population can be encapsulated within hydrogels, using standard encapsulation techniques. Alternatively or additionally, two different areas or compartments can be formed within the bioscaffold that contains distinct factors (e.g., morphogens, growth factors, adhesion ligands), or the material in a distinct form (e.g., varying mechanical properties or porosity). In some embodiments, the compartments can be fabricated individually, and then operably coupled to each other with any suitable method known in the art such as use of an adhesive or exploitation of the intrinsic adhesiveness of each compartment, polymerization or cross-linking of one compartment to another and so forth. The scaffold can be designed to have a number of compartments or areas in which cells enter in parallel and distribute according to their characteristics (e.g., size or mobility), serially pass through all or some of the compartments, or a combination of both. The different compartments can even be construed to induce distinct fates for the contained cells during the passage therein.

During or after the manufacturing process, the scaffold material can be functionalized with additional elements such as for instance bioactive molecules. Said elements can be coated on or embedded within the bioscaffold with any suitable means known in the art, either in a homogeneous or non homogenous manner and can provide additional functional properties to the material such as enhanced/reduced biodegradation, physical stabilization, biological activity and the like. As used herein, a "bioactive molecule", as well as "(bio)active compound" or "therapeutic agent", is any active agent having an effect upon a living organism, tissue, or cell. The expression is used herein to refer to any compound or entity that alters, inhibits, activates, or otherwise affects biological or chemical events.

One skilled in the art will appreciate that a variety of bioactive compounds can be used depending upon the needs. Exemplary therapeutic agents include, but are not limited to, a small molecule, a growth factor, a protein, a peptide, an enzyme, an antibody or any derivative thereof (such as e.g. multivalent antibodies, multispecific antibodies, scFvs, bivalent or trivalent scFvs, triabodies, minibodies, nanobodies, diabodies etc.), an antigen, a nucleic acid sequence (e.g., DNA or RNA), a hormone, an anti-inflammatory agent, an anti-viral agent, an anti-bacterial agent, a cytokine, an oncogene, a tumor suppressor, a transmembrane receptor, a protein receptor, a serum protein, an adhesion molecule, a lypidic molecule, a neurotransmitter, a morphogenetic protein, a differentiation factor, an analgesic, organic molecules, metal particles, radioactive agents, polysaccharides, a matrix protein, and any functional fragment or (chimeric) derivative of the above, as well as any combinations thereof. For "functional fragment" is herein meant any portion of an active agent able to exert its physiological/pharmacological activity. For example, a functional fragment of an antibody could be an Fc region, an Fv region, a Fab/F(ab')/F(ab')$_2$ region and so forth.

The bioactive compounds can be added to the scaffold material or to the polymeric gels by using any suitable method known in the art, such as surface absorption, physical immobilization, e.g., using a phase change to entrap the substance in the scaffold material, and the like. For example, a growth factor can be mixed with a polymeric (e.g. collagen) composition while it is in an aqueous or liquid phase, and after a change in environmental conditions (e.g., pH, temperature, ion concentration), the liquid gels or solidifies, thereby entrapping the bioactive substance. Alternatively, covalent coupling, e.g. using alkylating or acylating agents, is used to provide a stable, long-term presentation of a bioactive substance on the scaffold in a defined conformation. Alternatively, non-covalent adsorption can be used, for example electrostatic, hydrophobic, dipoledipole, hydrogen bonding, physisorption and the like. In an additional or alternative embodiment, bioactive molecules can be encapsulated within nano/micro spheres or beads included within the scaffold and/or a polymeric gel during or after a manufacturing step. Particularly suitable nano//micro beads are those described in European Patent Application EP15193284.5, incorporated herein in its entirety by reference.

The scaffold material described herein is useful in the treatment of a variety of diseases, disorders, and defects where surgery or a tissue engineering approach can be a suitable therapeutic solution. This is particularly true for soft tissues, and the scaffold material may therefore be utilized in a variety of surgical procedures as well as for cosmetic purposes, and for the treatment or prevention of a plethora of pathological conditions. The scaffold material of the invention results particularly convenient for treating tissues or organs like a genitourinary tract components, including kidney, bladder, urethra, ureter, vaginal and pelvic floor tissue, a blood vessel (including big veins and arteries), a muscle, a cartilage, skin, liver, an eye portion such as cornea, conjunctiva or sclera, a Central Nervous System (CNS) or Peripheral Nervous System (PNS) component including cerebral or meningeal tissues, trachea, oesophagus, lungs, stomach, heart, sphincters, pancreas, gut, pharynx or inner ear tissue.

The scaffold is usually transplanted on or close to a target tissue, introduced into or onto a bodily tissue/organ of a subject or a host using a variety of methods and tools known in the art, preferably via minimally invasive surgical devices and procedures.

The term "subject" or "host" as used herein refers to animals, particularly to mammals. For example, mammals contemplated by the present invention include humans, primates, pets, domesticated animals such as cattle, sheep, pigs, horses, rabbits, rodents and the like.

As used herein, "treatment", "treating" and the like generally mean obtaining a desired pharmacological and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" or "treating" as used herein covers any treatment of a disease in an animal, particularly in a mammal, more particularly a human, and includes: (a) inhibiting the disease, i.e., arresting its development; or (b) relieving the disease, i.e., causing regression of the disease and/or its symptoms or conditions such as improvement or remediation of damage. The term "prevention" or "preventing" relates to hampering, blocking or avoid a disease from occurring in a subject which may be, for any reason, predisposed to the disease but has not yet been diagnosed as having it for example based on familial history, health status or age.

Figure 2:
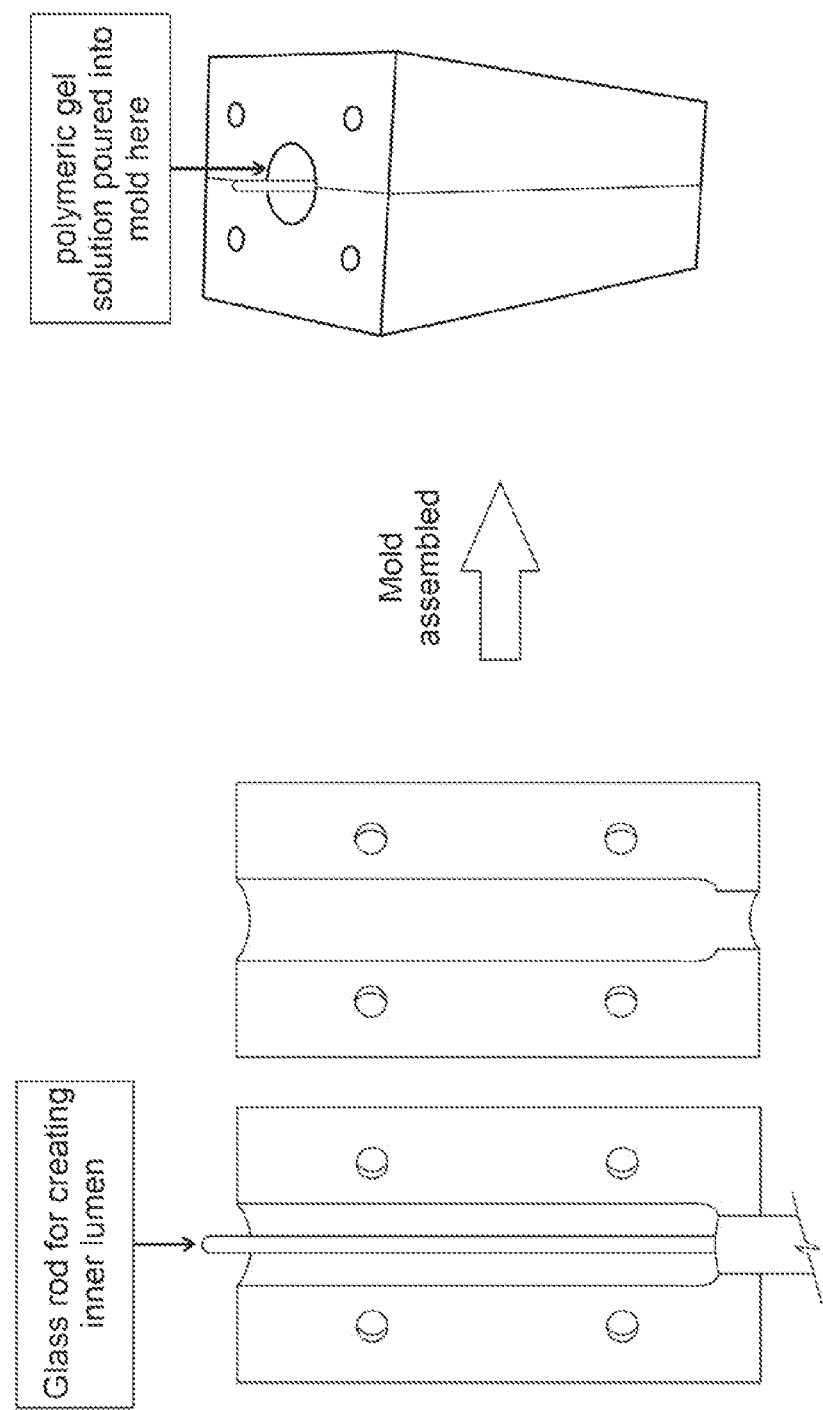
FIG. 2 shows one embodiment of a mold used to produce a polymeric tubular scaffold with an inner lumen.

Initially, the method for producing the scaffold of the invention foresees a first fast drying step via a mechanical compression of a polymeric gel, preferably hydrogel, layer (FIG. 1A). It has been assessed that this first step of mechanical compression allows to achieve a non-uniformly stiff micro/nano structure of the gel and, consequently, of the final scaffold. When working with polymeric gel layers in form of sheets, the mechanical compression is generally done by applying a rolling or linear compressive force, which must be orthogonal to the planar surface of the sheet. This latter is e.g. placed on a nylon mesh positioned on tissue paper to augment the water absorption upon leakage following the compression. When working with polymeric gel layers already in form of tubes (FIG. 1B), these latter can be rolled against an adsorbent tissue, with or without e.g. a nylon mesh positioned in between, via e.g. a glass rod or otherwise a cylindrical mandrel placed within the lumen of the tube, until no more water is seen on the tissue paper, for instance by performing 10 revolutions of about 30 seconds each on the tissue paper. In some embodiments, an additional filtration step to mechanically suck water from a filter in contact with the lumen can be performed. Tubular polymeric single layers can be obtained by pouring a polymeric gel precursor solution into a substantially cylindrical mould comprising therein a removable, coaxial elongated support (e.g. a glass rod) of any suitable diameter so to create a void space, the tube's lumen, upon formation of the polymeric gel (through e.g. gelation of the precursor solution; FIG. 2).

A key feature of the method according to the invention relies in a second, slow drying step of the polymeric gel in order to obtain the final single layer polymeric scaffold. This step envisages the use of techniques such as water filtration or preferably air drying, as well as combinations thereof, for gradually and gently reducing the water content of a polymeric gel up to a polymer mass fraction in the final scaffold of at least 60% w/w. Preferred water filtration means can be for instance dialysis means. In the most preferred embodiment, the method is characterized in that the second slow drying step is performed by air-drying under gravity for at least 1 hour, preferably for at least 4 hours. The air drying process is preferably carried out at room temperature (i.e., between about 20° and about 30° C.), and in some embodiments in a controlled atmosphere to keep sterility of the final scaffold. Once obtained a single layer polymeric scaffold, this can be possibly circumferentially wrapped around a suitable support of any shape, such as for instance a removable glass rod, in order to realize a tubular Collagen scaffold comprising a lumen therein.

The so-obtained slowly-dried scaffolds feature peculiar characteristics both in terms of mechanical values when they are sutured in a surgical approach, as well as for what concern tissue regeneration and healing in a host, compared to solutions known in the art. In fact, the scaffolds of the invention offer an excellent compromise between these two issues, that must contemporary be considered when it comes to the clinics. Current clinically used natural materials sold as off-the shelf solutions include for instance freeze-dried collagen scaffolds, cross-linked collagen scaffolds and decellularized human and animal tissue-derived scaffolds. These products are designed with a surgical mind set of being easy to surgically work with. The scaffolds of the invention, on the other hand, are strong enough to be sutured while providing in parallel a more "cellular friendly" matrix, compared to the commercially available solutions, i.e. surgeon-friendly and stiff scaffolds with poor cellular responses. As a way of example, commercially available tubular acellular materials do not work in urethral replacement of length defects longer than 1 cm; if cells are placed within these commercial available materials they can achieve successful grafts for patients. On the other hand, the present collagen-made scaffolds produced according to the methods of the invention show successful results with 1 cm long or even bigger (e.g., 2 cm long) tubular grafts without the addition of any cells. In the same way, planar scaffolds such as sheets or patches sized at least 1 cm$^2$ can be successfully used in vivo.

In this context, without being bound to this theory, the present inventors observed that very mechanically stable donor tissues, which has been decellularized or devitalized to not elicit immune response in the graft host patients, are too stiff, or otherwise not enough soft, to give a functional repopulation of the grafted scaffold by host cells. The extreme internal complexity and/or density creates a sort of "extracellular matrix (ECM)-mismatch" between the grafted matrix and the injured/tissue regeneration site. This mismatch is plausibly the cause for an ill-favoured cell ingrowth, leading to failure of the therapy for the patients. The scaffold of the invention targets instead a novel "Mechanical and ECM-complexity niche": it is structurally less complex, less stiff, less dense and therefore easier to be invaded by endogenous host cells without giving strong inflammatory response, thus favouring a better and accelerated regeneration profile than other materials, but still easily suturable. The method of the invention allows to produce scaffolds targeting this specific "Mechanical and ECM-complexity niche".

For instance, in the case of the urinary tract, the scaffold's surface stiffness favours a better and faster urothelial coverage, which is probably linked to a better protective environment for sub-urothelial tissue regeneration (like muscle and vascular regeneration). Without being necessarily bound to this theory, at least one layer in the scaffold shall lay close to native adult tissue in terms of mechanical properties for having a better surgical experience, but a major component should be protected to be soft. This could explain why decellularized native tissues, having mechanic properties very close to those of native adult tissues, fail or do not have perfect results; mimicking the mechanics of early development tissues, at least on portions of a scaffold material, could be physiologically more fitting and "better sensed" by a receiving host. In this context, in preferred embodiments of the invention, the stiffer portion of the polymeric scaffold should have a retention strength of at least 0.2 N upon suture, preferably of at least 0.4 N, even more preferably with values comprised between about 1.5 and 2 N.

Figure 5:
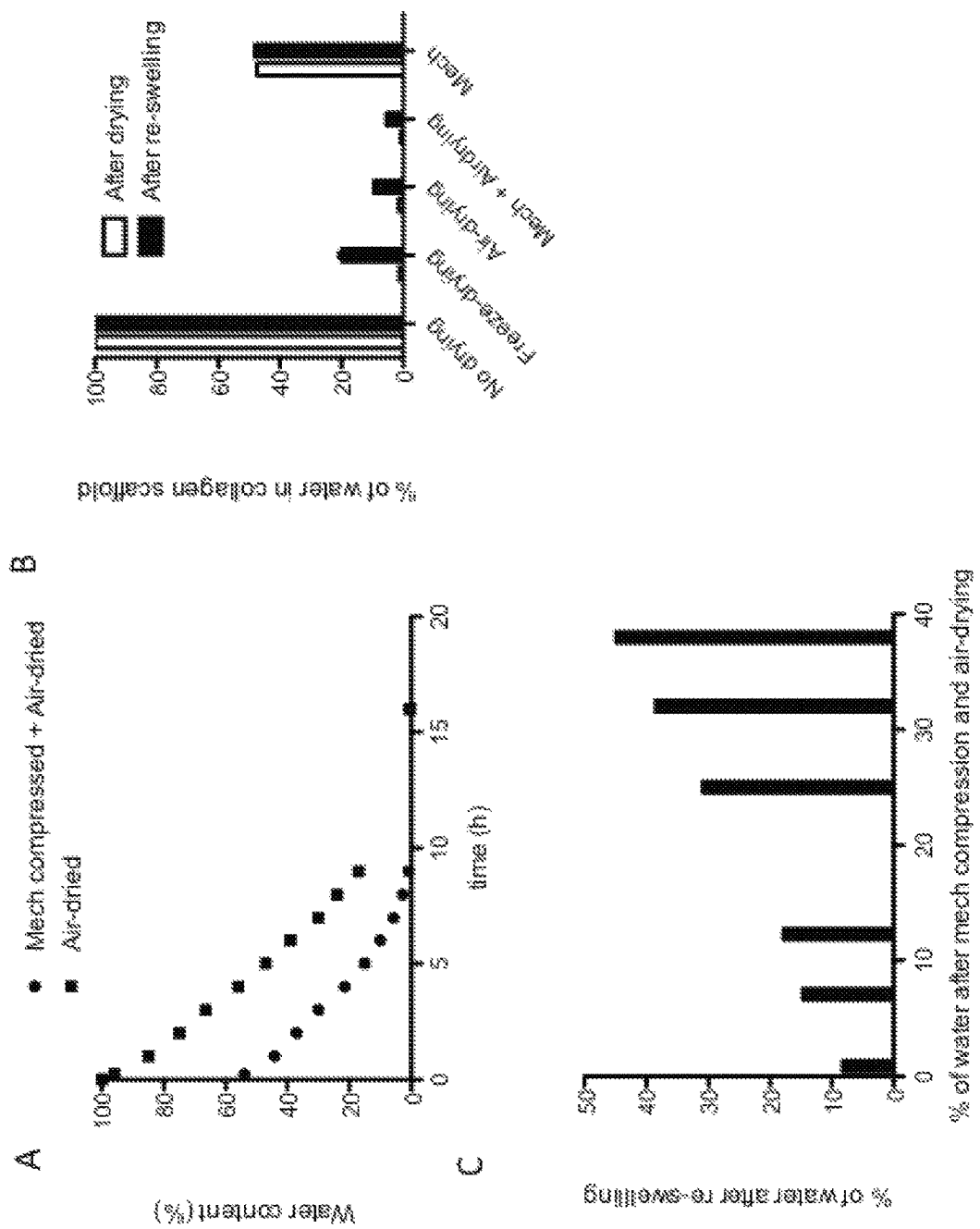
FIG. 5 shows the influence of the drying method and the final drying state on the re-swelling behaviour of collagen scaffolds. (A) Mechanical compressed followed by air-drying is compared to only air-drying of collagen, with monitoring of the water content and time of air-drying. There is a clear trend in the time of air-drying and water content (B) No drying of produced collagen scaffolds results in a 100% water content in the collagen scaffold (white bars after drying), and the water content does not change upon incubation in a hydrating environment (black bars after re-swelling). Utilizing the method of freeze-drying to reduce water content in the collagen scaffold results in a dried scaffold with an average of 1.3% water content, and reaches an average of around 20% water content after re-swelling. Utilizing only air-drying allows obtaining an average dry level of 1.5% water content that increases to 9.5% after re-swelling. Utilizing mechanical compression with air-drying allows obtaining an average of 0.8% water content that increases to 5.2% after re-swelling. Utilizing only mechanical compression allows obtaining an average dry level of 47.6% water content that increases to 48.3% after re-swelling. (C) The air-drying method can be used to manipulate the re-swelling behaviour of collagen scaffolds by changing the final dry-state (% water); A linear trend between the final dry-state of the collagen scaffold and the degree of re-swelling is observed; At least 1 h of air drying after mechanical compression yields a different material with different water content compared to only a mechanical compressed scaffold.

In terms of swelling behaviour, which then also reflects the mechanical properties of the scaffold of the invention (water content in polymeric scaffolds are known to be related to the mechanical properties, i.e. the more water content the lower mechanical strength), it has been surprisingly assessed by the inventors that the scaffolds produced with the present methods, when immersed in an aqueous solution such as Phosphate buffered saline (PBS), re-swell and increase their water content only to up of a maximum of 12% w/w at steady state. Compared to other manufacturing techniques, this has important advantages in terms of functional and mechanical properties of the final scaffold: by applying a fast mechanical compression to a first polymeric gel followed by a slow drying step, a scaffold ready to be sutured can be easily achieved. In comparison, a freeze-dried collagen gel swells and increase its water content to more than 20% w/w (FIG. 5B). Mechanically compressed collagen gel swells and increases its water content only by 0.7%. Substantially, the developed method permits to better control the re-swelling behaviour of the obtained scaffold, and then ultimately the mechanical and functional properties ideal for surgery.

This property represents moreover a huge advantage for what concerns the stocking and the packaging of the scaffold of the invention, since it could be provided to a surgeon as an off-the-shelf, ready-to-use solution. In fact, it can be imagined a polymeric scaffold of the invention prepared and packaged in a liquid/aqueous solution already adapted for use in an in vivo approach, without any change in its properties at steady state even when hydrated. The "re-swelling steady state" is defined as the state in terms of water content of the polymeric scaffold produced with the methods of the invention in which the mechanical properties and the water content of the said scaffold do not change anymore.

With the aim of accentuating the mechanical differences between two different areas of a polymeric scaffold of the invention, the inventors developed a very ingenious and elegant method for producing non-uniformly stiff scaffolds, said method being characterized in that it comprises the following steps:

a) providing a single layer of a mechanically compressed polymeric material gel wrapped around a support;

b) dipping a portion of the support-wrapped polymeric gel layer into an aqueous solution while leaving another portion air-drying under gravity for a certain amount of time;

c) flipping the polymeric gel layer portion previously dipped into the aqueous solution onto the air-dried portion; and d) optionally air-drying under gravity both layers for a certain amount of time wherein at least one layer of the so obtained polymeric scaffold has a polymer mass fraction of at least 60% w/w. This method, renamed by the inventors "the sock-technique" and shown in FIGS. 4 and 5, can be applied, mutatis mutandis, to polymeric gels formed by e.g. pouring a polymeric gel precursor solution into a substantially cylindrical mould comprising therein a coaxial elongated support for creating a tubular single layer of polymeric gel, gelling it and mechanically compress it.

An additional object of the invention relates to a kit comprising a container, an aqueous solution and the polymeric scaffold of the invention. The three components can be provided separated within the kit, or the container can already include the liquid solution and also possibly the polymeric scaffold in a re-swelled, steady-state form. Preferably, the entire kit is sterilized or sterilisable by electrode beam, gamma rays or X-rays radiations.

EXAMPLES

The present, non-limiting examples present one embodiment of the fabrication method of a non-uniformly stiff tubular collagen scaffold according to the invention. The method can be easily adapted to make sheet and dome-shaped structures, and dimensions and shape of the collagen scaffold depend only of the used mold. For the fabrication of a tubular non-uniformly stiff collagen scaffold with an inner lumen of 3 mm, 8.5 mL of liquid acido-soluble bovine collagen solution (5 mg/mL, Symatese, France) are mixed with 0.8 mL 10× MEM (Invitrogen) and neutralized by the addition of approximately 1.85 mL of 0.1M NaOH. The exact volume of NaOH to be added is determined by observing a colour change from yellow to pink. The neutralized collagen solution is poured into a tubular shaped, stainless steel mould (length 70 mm, inner diameter 12 mm). The lumen of the tubular collagen scaffold is formed by a glass stick (diameter 3 mm) placed inside the tubular mould. Collagen gelation takes place at room temperature for 15 min. After gelation, the collagen tube is removed from the mould but kept on the glass stick. This gelated collagen tube is the starting matrix to produce non-uniform (denser external walls and a less dense internal side) tubular collagen scaffolds.

The tubular collagen gel is mechanically compressed by rolling on around its own axis, to ensure unequal compression and drainage of water within the final scaffold. The collagen gel is rolled over a nylon mesh placed on five layers of double-layer tissue paper (Weita, Arlesheim, Switzerland) until no more water is coming out. Subsequently, a further drying step is performed by exposing the collagen tube to air at room temperature for 1 to 24 hours. The desired dryness corresponds to 0.5-40% of the initial water content of the gel, preferably 18-22% of water. The weight of the collagen gel after gelation represents 100% of water. The percentage of water in each dried collagen scaffold is calculated by taking the difference of the collagen gel weight before and after drying:

% of water=1−[(weight before drying-weight after drying)/weight before drying]

Once the collagen tube has reached the desired dryness, the tube is placed in PBS (pH 7.4) for 3 days in order to re-swell it to a steady-state water content. The water content of the final collagen scaffold is in the range of 5 to 48%, preferably 24-30% of water content.

For the fabrication of a multi-layered collagen tube through the "sock technique", half of a tube dried with a first rolling step as previously described is placed into a rehydration bath (PBS, pH 7.4) for 1 to 60 minutes, preferably for 30 minutes. The rehydrated half tube is then pulled over the dried tube portion or the dry portion is pushed under the rehydrated part for creating a multi-layered tube. Multi-layered tubes (with more than two layers) can be obtained by iterating the above described steps.

Ultimate tensile strength (UTS) and Young's modulus were determined under stress strain conditions using an Instron tensile machine (Norwood, Mass., USA), applying a 250 N load with a strain rate of 1 mm/min until the break point. Tubular samples of 5 mm length was pulled from the lumen side in one direction using L-shaped hookes placed in the lumen. Young's modulus values were obtained from the slope of the initial linear region of the stress-strain curves, while the UTS were obtained from the maximum tensile stress recorded.

To determine the collagen density and porosity in the scaffolds, scanning electron microscopy (SEM) was performed. The samples were fixed with 1% tannic acid and 1.25% glutaraldehyde, then washed with 0.1 M cacodylate, and dehydrated in increasing ethanol concentrations prior to critical point drying (CPD). They were coated with gold/palladium and imaged at a voltage of 10 kV using a scanning electron microscope (SEM, XLF30, Philips). To further visualize the collagen density and porosity within the scaffolds, formalin fixed (4% PFA) and paraffin embedded cut sections (8 μm thick) were stained with anti-collagen type1 antibodies (1:250 dilution, rabbit anti-collagen type 1, Abcam, Switzerland). Corresponding secondary AlexaFluor antibodies (Abcam, Switzerland) were used to visualize the type 1 collagen distribution under a LSM700 microscope (Zeiss, Germany).

To determine the in vitro suture capacity, anastomosis of two produced collagen tubes was performed using Vicryl 6.0® sutures. Furthermore, to determine the in vivo suture capacity of the produced tubes, at least 9 rabbits had a urethral replacement surgery, where a double end-to-end anastomoses to the native urethra were performed with interrupted sutures (Vicryl 6.0®). Rabbits were sacrificed after 1 and 3 months. Thereafter, rabbit penises were harvested and fixed in 4% formalin, embedded in paraffin, and sectioned in 8 μm thick for Hematoxylin-eosin staining. Images were taken with a Leica DM5500 microscope (Germany).

To understand different cell type behaviour (e.g. urothelial and smooth muscle cells) on various collagen-based scaffold with different stiffness and collagen fiber densities, human urothelial cells that were lentiviral-transduced with GFP were seeded onto these collagen scaffolds and cell morphology was observed under a fluorescence stereomicroscope (Leica). The human cells were placed in a fibrin drop to control the spatial distribution of cells on the collagen, and the cells at various time points were then imaged to verify the cells fate choices.

Results

Figure 6:
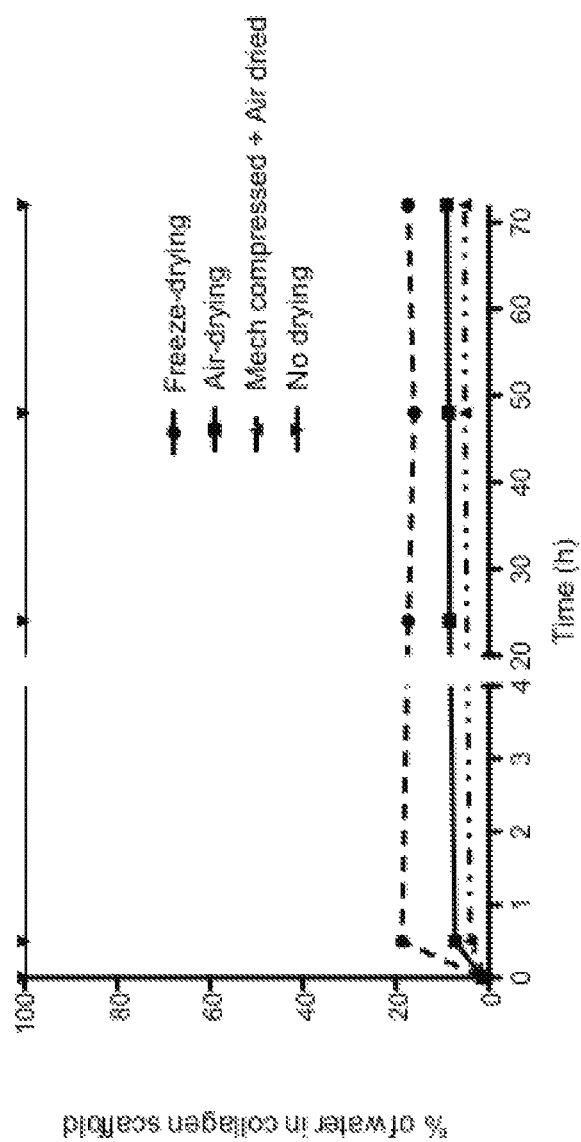
FIG. 6 shows the re-swelling steady state of collagen scaffolds. Freeze dried, air-dried, and mechanically compressed with air-dried collagen scaffolds rapidly re-swell (within 30 min) in a hydrating environment. A steady-state re-swelling is occurring within 72 h in hydrating conditions.
Figure 7:
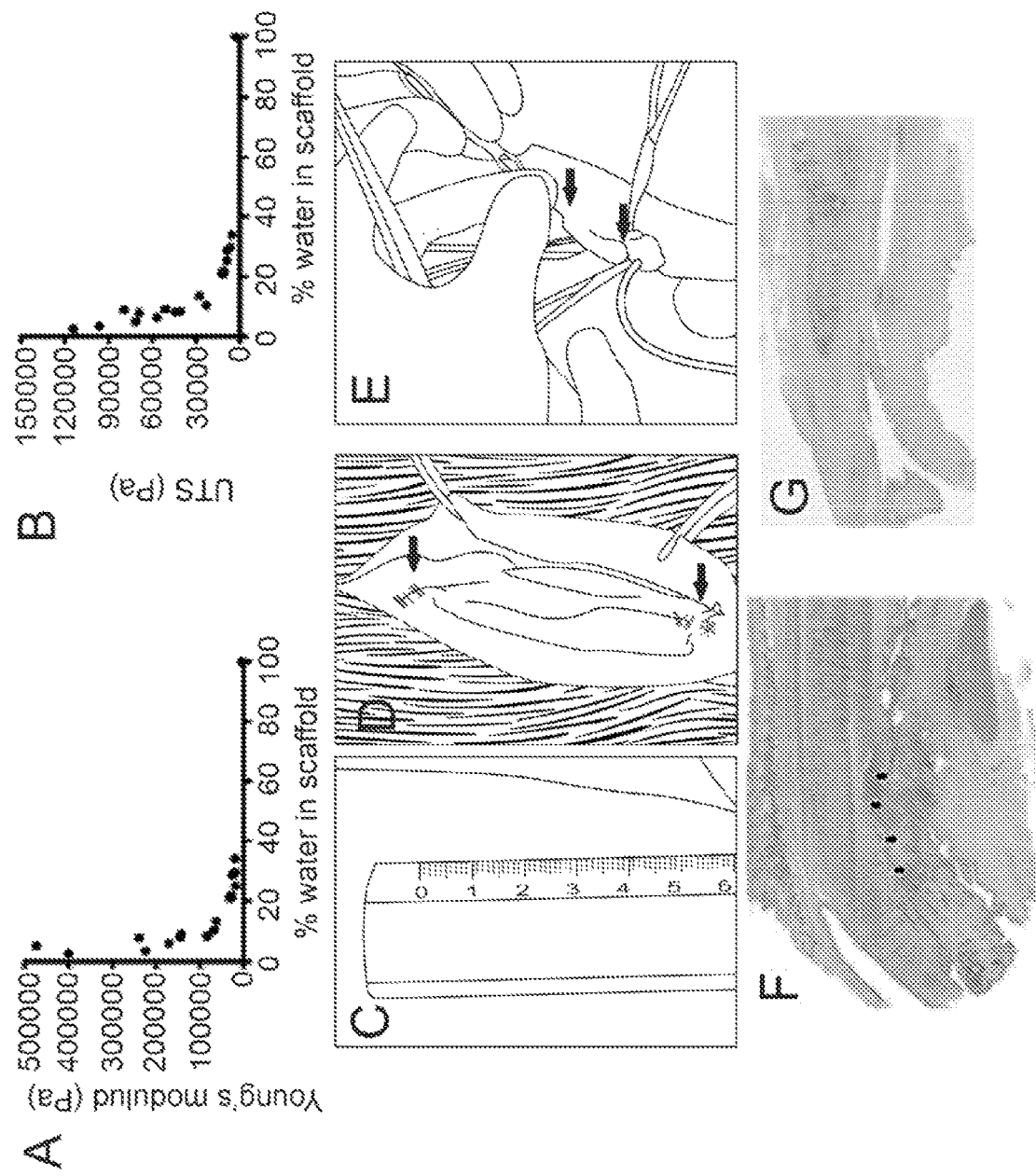
FIG. 7 shows the relation between the mechanical properties and percentage of water present within surgery-compatible collagen scaffolds. (A and B) Air-dried collagen scaffolds show that water percentage is a crucial parameter for the mechanical properties (Young modulus and Ultimate tensile strength) of the scaffold. (C and D) An air-dried (1.5% water content) and re-swelled collagen scaffold (9.5% water content) is anastomosed to a goat urethra using Vicryl 6.0 sutures. (E) Even a mechanical compressed plus air-dried for 1 h (38% water content) and re-swelled collagen scaffold (45% water content) is anastomosed to a dog urethra using Vicryl 6.0 suture. (F and G) Hematoxylin & eosin staining of tissue samples harvested 1 month and 3 months after surgery in rabbits. White arrows show the sutures and black arrows point to the remaining collagen of the implanted scaffold that is slowly being replaced by host tissue and finally completely disappeared 3 months post-surgery.

First of all, mechanical compression with air-drying and only air-drying yields different materials, as seen in FIG. 5A it also takes longer time to reach different dry states for only air-dried material compared to mechanical compression with air-drying. A fast compression yields less re-swelling compared to the other method of slow drying. As shown in FIG. 5B, the collagen scaffolds dried with either freeze-drying (FD) air-drying (AD) or mechanical compression with air drying (M-AD) re-swell when they are placed in hydrating conditions (FD dry: 1.3% to FD re-swell: 20%, AD dry: 1.5 to AD re-swell: 9.5%, M-AD dry: 0.8% to M-AD re-swell 5.2% water content). However, mechanically compressed (M) have a very low swelling capacity when placed in hydrating conditions (M dry: 47.6% to M re-swell: 48.3% water content). Furthermore, the mechanical compressed plus air-dried collagen scaffold's re-swelling can be controlled by its dry state, as shown in FIG. 5C. There is a linear relationship between the dry state and the re-swelling state of the produced collagen scaffolds. The re-swelling in hydration (in PBS-bath) is a rapid process where most of the swelling has occurred within the first 30 minutes (FIG. 6). A more stable re-swelling steady-state is seen after 72 h in a hydrating environment. The mechanical properties, Young's modulus and UTS of the collagen scaffolds with different water contents follow an exponential curve (FIGS. 7A and 7B). As shown in FIGS. 7C and 7D, the collagen tube dried and re-swelled to a 9.5% water content is sutured with ease into rabbits and goat urethra's (goat urethra is shown in FIG. 7D). Also the re-swelled collagen scaffold of 45% water content is sutured to rabbit and dog urethra (dog urethra surgery is seen in FIG. 7E). Classifying what is suture compatible is difficult since it is highly dependent on the surgeon, and can only be done on an empirical basis. However, starting from the mechanical properties recorded and surgeons opinion when handling the collagen grafts of different water content, a material that has a dry state of at least one collagen layer of no more than 40% w/w water content (i.e., at least 60% w/w collagen mass fraction) was classified as suture compatible directly after it has been re-swelled to steady-state in hydrating condition, when produced from a mammalian collagen precursor liquid solution with range of collagen concentration comprised between 2.1 and 40 mg/mL.

The high functional regeneration potential of the scaffold of the invention is highlighted in a surgical setting where collagen tubes produced according to the methods of the invention were implanted and sutured in a rabbit urethra. The collagen scaffolds stay in the sutured area as shown in a histology section of 1 month after surgery (FIG. 7E), black arrows show non-degraded collagen from remaining parts of the collagen scaffolds). After 3 months, no more of the implanted collagen can be visualized by histology, since the rabbits' own cells have remodelled the collagen and populated the area (FIG. 7F).

Figure 8:
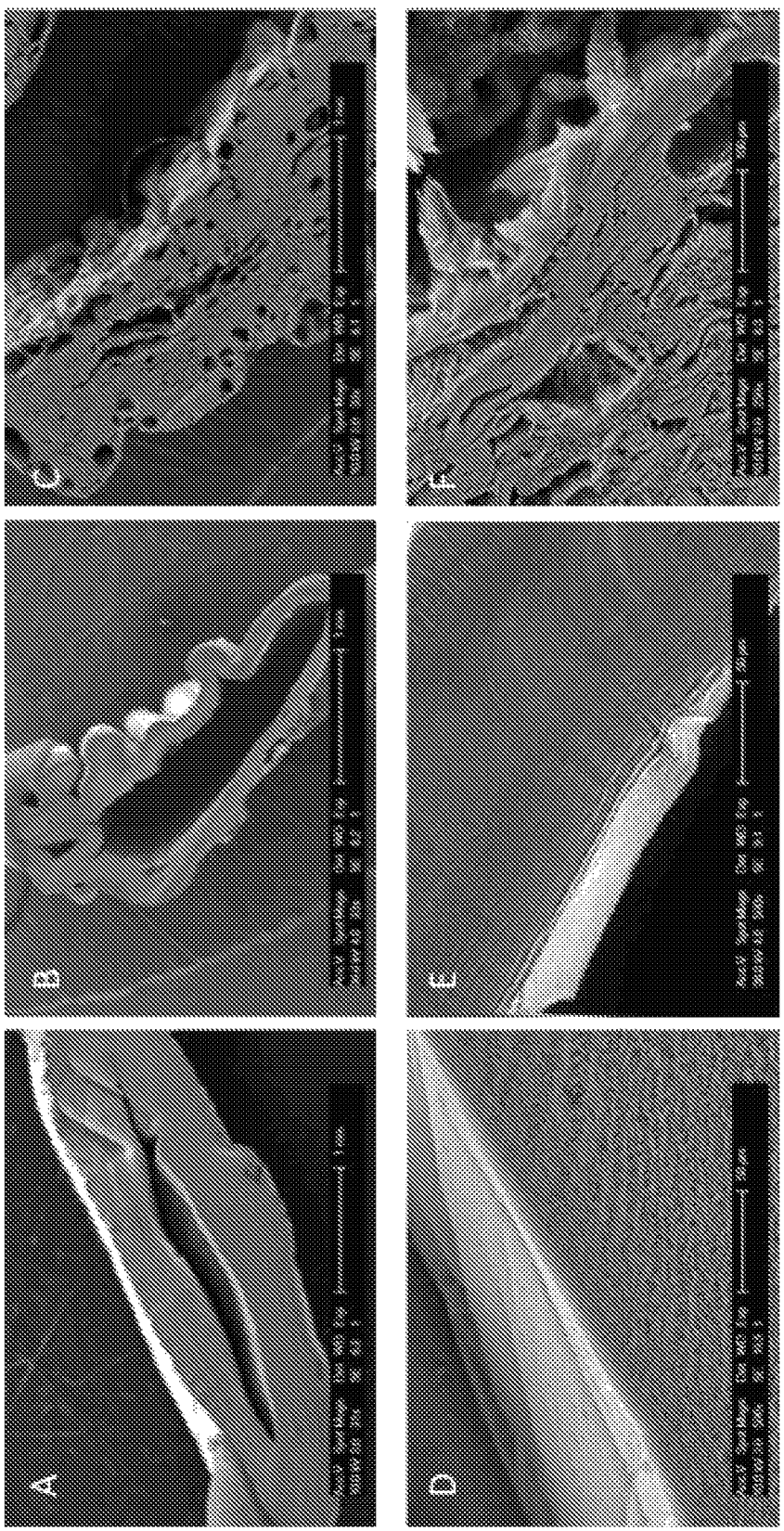
FIG. 8 shows the microscopic collagen structure at the micro-nano scale after different drying methods. A and D show a collagen tube produced by mechanical compression (plastic compression) followed by air drying (semi-elastic compression) yielding a heterogeneous or "non-uniform" collagen structure. The non-uniform structure is the result of the application of two different drying methods during the fabrication procedure. B and E shows a collagen tube that has only been air-dried yielding a homogenous or "uniform" collagen structure. C and F show a collagen tube that has been freeze-dried yielding a random, non-uniform collagen structure, with pronounced holes distributed randomly in the collagen network.
Figure 9:
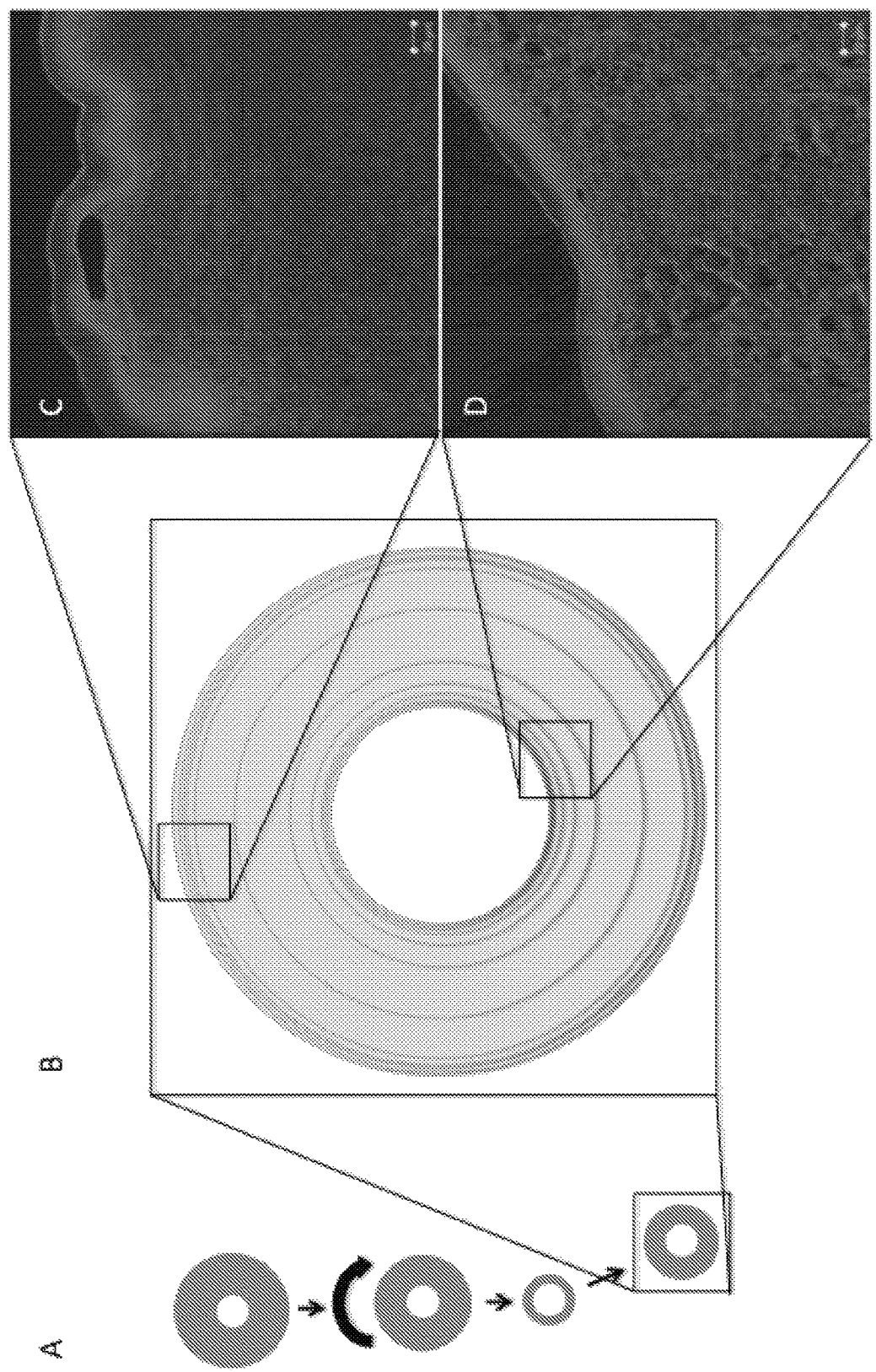
FIG. 9 visualizes the different collagen areas present within a tubular scaffold that was produced by applying both compressions, the plastic (mechanical load) and the semi-elastic (air-drying) one. (A) Schematic description of the manipulations to obtain a non-uniformly stiff tubular collagen scaffold. (B) Schematic representation of the collagen structure of the final tubular scaffold. (C and D) Immuno-histochemistry using anti-collagen type 1 antibodies on samples of a tubular bovine collagen scaffold to visualize the collagen type 1 fiber density. Images taken under a LSM700 confocal microscope (Zeiss) visualize the surface of the inner lumen (D) and the outer side (C) of a cross-section of a collagen tube.

A crucial observation done by the inventors is that a slow-drying procedure creates an uniform and homogenous collagen architecture at micro- and nanoscale (FIGS. 8B and 8D). While a freeze-dried collagen structure yields an unorganized non-uniformed architecture with random distribution of holes (diameter of 50-150 μm) (FIGS. 8C and 8F) at micro and nanoscale. In comparison, if one combine a first mechanical compression followed by a slow-drying step, this yields to a non-uniform but organized heterogeneous collagen architecture at micro- and nanoscale, where the surface that is in close contact with the mechanical force gets a more dense structure as compared to the internal side (FIGS. 8A and 8C). In FIG. 9, the same feature is shown by utilizing immunohistochemistry to visualize collagen type1.

Figure 10:
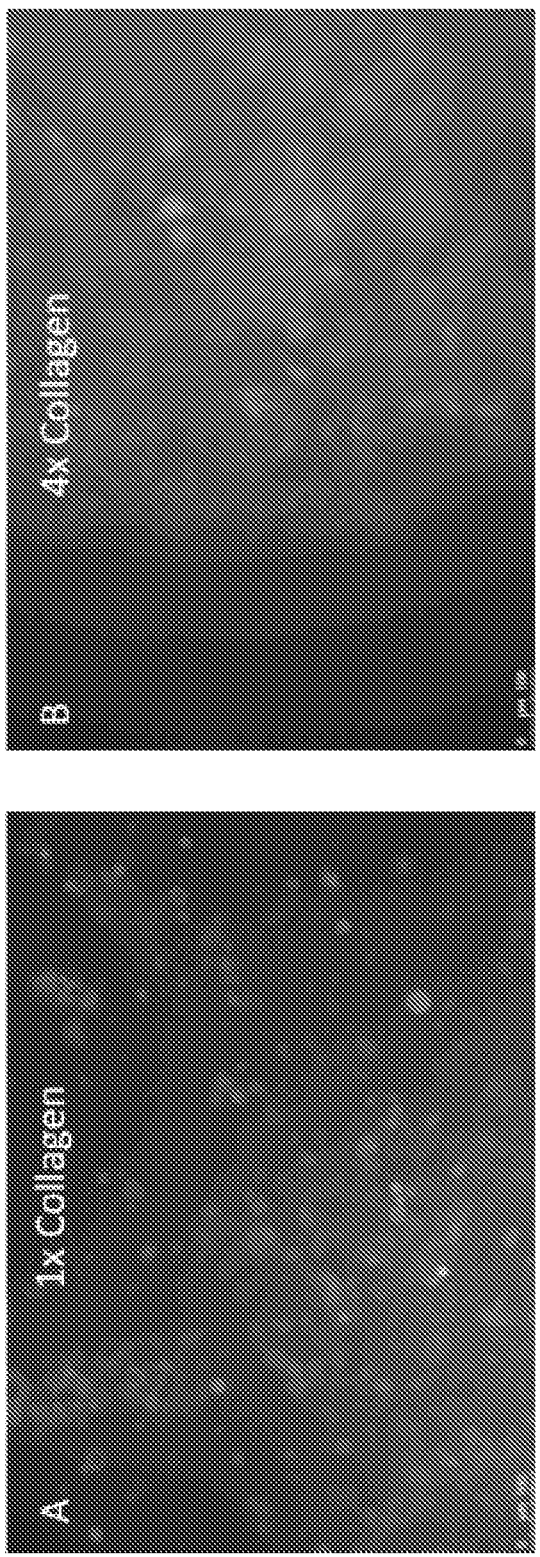
FIG. 10 shows the morphology of urothelial cells cultured on collagen scaffolds with different densities. GFP-lentiviral transduced urothelial cells were used to easily visualize them under a fluorescence stereomicroscope (Leica). 24 h after cell seeding, urothelial cells growing on (A) less dense collagen scaffolds form more single units and less connected colonies as compared to (B) urothelial cells growing on higher density collagen gels.

Many studies report that material stiffness, fiber density and porosity influence cell fate choices, and that different cell types behave differently by changing the material properties. FIG. 10 depicts the behaviour of urothelial cells in response to collagen matrices that differ in stiffness. In a less dense collagen matrix, the urothelial cells are less in contact with neighbours and migrate away from their starting position. On the other hand, urothelial cells seeded on a denser scaffold stay more in contact with neighbour cells and migrate less.

Figure 3:
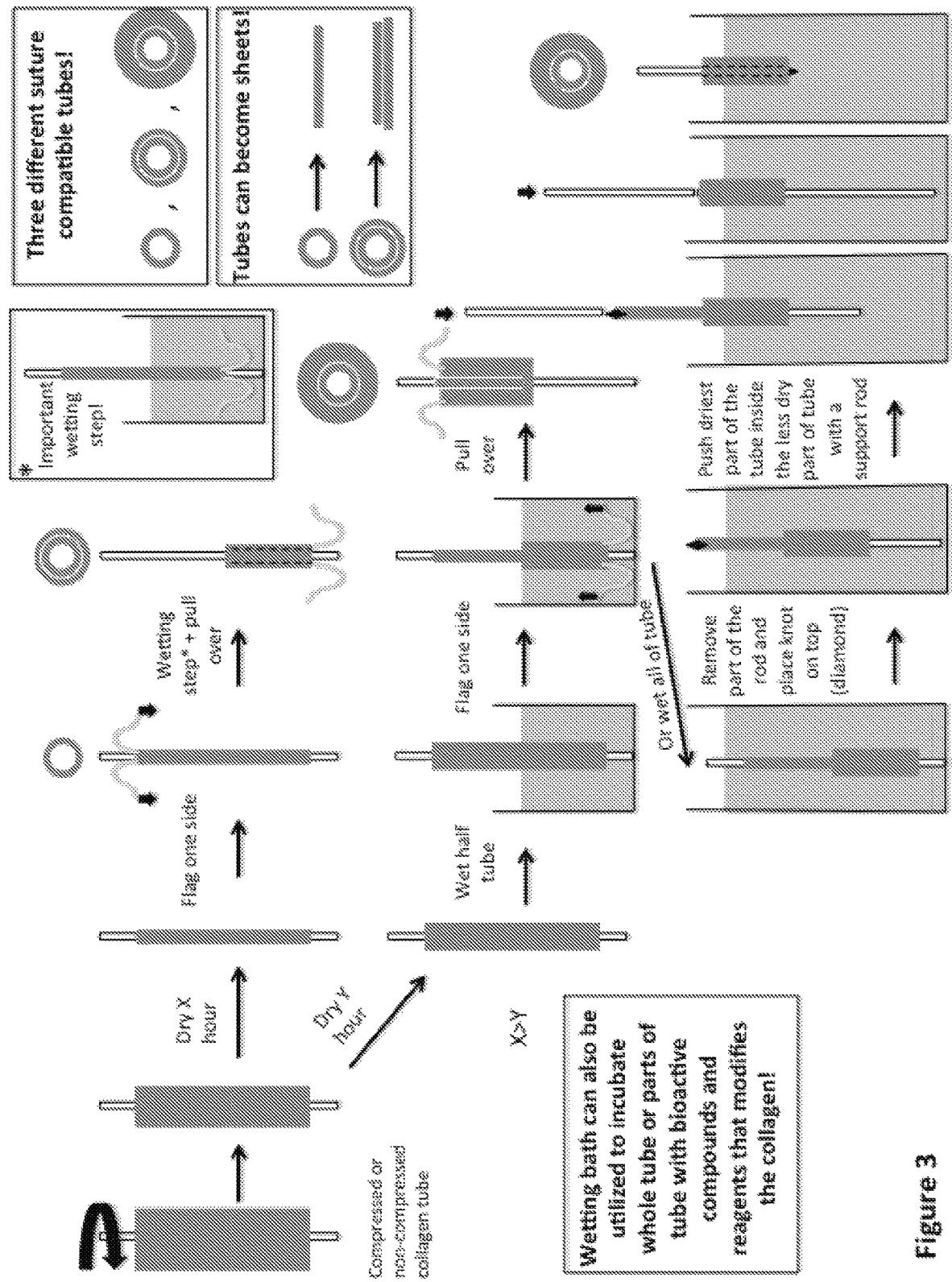
FIG. 3 shows a schematic representation of the "sock technique" according to the invention for producing non-uniformly stiff polymeric scaffolds.
Figure 4:
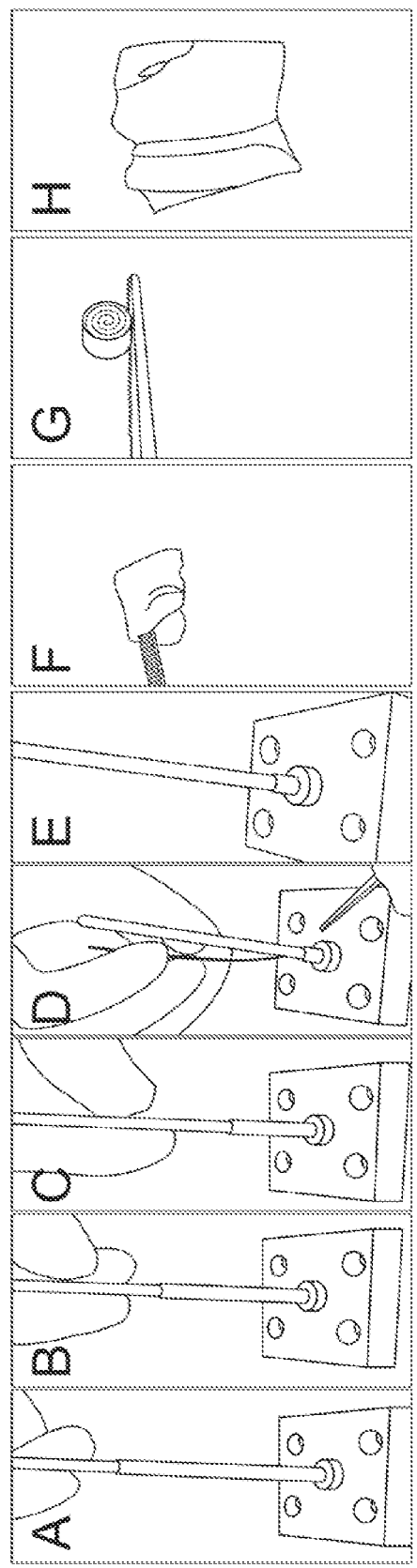
FIG. 4 shows images of the "sock technique" and the final structure of a double-layered and a single-layered collagen tube, as well as a collagen sheet obtained by opening of a double-layered tube. (A) The upper half of a collagen tube is hydrated. (B-E) The hydrated collagen half is pulled over the dry half. (F) A single layered suture compatible collagen tube on a forceps. (G) A double-layered suture compatible tube on a forceps. (H) The opened up double-layered tube forming a double layered sheet.

To further increase mechanical stability and the potential for creating non-uniformly stiff materials, with an option of spatially distribute growth factors and reagents to modify the collagen at various position in a scaffold, a further method, shown in FIG. 3, was developed. It describes a "sock-technique", taking advantage of the drying and swelling behaviour of the collagen described before. Various manipulations can be performed in order to get a structure with single layers or multiple layers, by pulling or pushing over a wetted structure on top of the other. In FIG. 4 it is shown the technique and the final structure of a double-layered and single-layered tube, wherein the former is clearly more stable since it can hold its own weight without having the lumen collapsing. Furthermore, tubes produced in this way can also be opened up by e.g. blade cut, resulting in single- or multi-layered sheets, which can be used as patches for surgical use. A double-layered sheet, originating from an opened double-layered tube using a scissor, is shown in FIG. 4H.

Additionally, the bioactivity of the non-uniform collagen scaffolds could be enhanced by the addition of bioactive molecules to the rehydration bath using one of the known platforms to efficiently bind bioactive molecules to collagen resulting in a controlled release from the collagen scaffold.

Collagen scaffolds prepared according to the described method are highly useful for soft tissue engineering or surgical applications of organs/tissues such as genitourinary system (i.e. for bladder augmentation, vaginal and pelvic floor reconstruction, ureter and/or urethra reconstruction), for vascular tissue engineering, for the reparation of the oesophagus or as patches for hernia repair.

The invention claimed is:

1. A method for producing a polymeric scaffold having a non-uniform density for use in tissue engineering, diagnostics or surgical procedures, wherein the method comprises the steps of:
   a) providing at least one layer of a polymeric material gel, the polymeric gel obtained from a collagen gel precursor solution having a collagen concentration between 2.5 mg/mL and 40 mg/mL;
   b) performing a first fast drying step by applying a mechanical compression on the polymeric material gel layer; and
   c) performing a second slow drying step of the gel up to reach a polymeric material mass fraction of at least 60% w/w, the step being performed by water filtration, air-drying, or a combination thereof,
   wherein the polymeric scaffold has a density at a surface that is denser as compared to a density at a core.

2. The method of claim 1, wherein water filtration is performed by dialysis.

3. The method of claim 1, wherein air-drying is performed under gravity for at least 1 hour.

4. The method of claim 1, further comprising the step of circumferentially wrapping the polymeric scaffold around a support in order to have a tubular polymeric scaffold comprising a lumen.

5. The method of claim 1 wherein the layer of polymeric material gel is tubular and obtained by first pouring a polymeric gel precursor solution into a substantially cylindrical mould comprising therein a coaxial elongated support for creating said tubular single layer of polymeric material gel.

6. The method of claim 1, wherein the polymeric material is natural polymeric material or an extra-cellular matrix (ECM)-derived polymeric material.

7. The method of claim 6, wherein the natural polymeric material or ECM-derived polymeric material is gelatin, elastin, laminin, collagen, agar/agarose, chitosan, fibrin, proteoglycans, a polyamino-acid or a derivative thereof, polylysin or gelatin methyl cellulose, carbomethyl cellulose, polysaccharides and a derivatives thereof, glycosaminoglycanes including at least one of hyaluronic acid, chondroit-insulfate, dermatansulfate, heparansulfate, heparine, keratansulfate or alginate, or any combination thereof.

8. The method of claim 1, wherein no crosslinkers are added to the polymeric material gel.

9. The method of claim 1, further comprising a step of d) performing an in vitro hydration step with a cell-free aqueous solution where the scaffold re-swells with more than 4% w/w to reach a steady-stage water content in the scaffold.

10. The method of claim 9, wherein the steady-state water content is in the range of 5% to 48% w/w.

11. The method of claim 9, wherein the steady-state water content is in the range of 24% to 30% w/w.

* * * * *